United States Patent [19]  [11]  4,371,520
Uemura et al.  [45]  Feb. 1, 1983

[54] PROCESS FOR PREPARING IMMUNOGLOBULIN SUITABLE FOR INTRAVENOUS INJECTION

[75] Inventors: Yahiro Uemura; Takashi Goto, both of Hirakata; Yoshiaki Kano, Osaka; Satoshi Funakoshi, Katano, all of Japan

[73] Assignee: The Green Cross Corporation, Osaka, Japan

[21] Appl. No.: 316,042

[22] Filed: Oct. 28, 1981

[51] Int. Cl.³ ............................................. A61K 39/00
[52] U.S. Cl. ......................................... 424/85; 424/86; 424/87; 424/101; 260/112 B
[58] Field of Search ..................... 424/85, 86, 87, 101; 260/112 B

[56] References Cited

U.S. PATENT DOCUMENTS 4,165,370  8/1979  Coval ..................................... 424/85

Primary Examiner—Sam Rosen
Attorney, Agent, or Firm—Cushman, Darby & Cushman

[57] ABSTRACT

A process for preparing immunoglobulin suitable for intravenous injection, comprising treating with an acid a plasma or fraction I+II+III, fraction II+III, fraction II, or fraction III (hereinafter these are sometimes referred collectively to as starting material) obtained from plasma by Cohn's cold alcohol fractionation method, and subjecting to fractionation using an alkylene oxide polymer or copolymer having a molecular weight of 2,000 to 20,000.

8 Claims, No Drawings

PROCESS FOR PREPARING IMMUNOGLOBULIN SUITABLE FOR INTRAVENOUS INJECTION

This invention relates to a process for preparing immunoglobulin suitable for intravenous injection.

Since the immunoglobulin possesses antibody activity to many pathogens, it is administered to patients deficient in various antibodies to protect them from injection diseases or for the therepeutic purposes. The immunoglobulin preparations have been developed in two types, the one being for the intravenous injection and the other being for the intramuscular injection, and both are widely in clinical use.

The known methods for the preparation of intravenous administration type include that in which crude immunoglobulin is treated with proteases such as pepsin and plasmin, that which employs chemical modification of immunoglobulin by acylation and other chemical means, and that utilizing fractionation of the plasma or of Cohn's plasma fractions using polyethylene glycol, Pluronics (polyoxyethylene-polyoxypropylene copolymer), or the like.

In the immunoglobulin for intravenous administration obtained by the method of pepsin treatment, 7S IgG has been transformed into F(ab')$_2$ by the digestive action of pepsin, which has a disadvantage of very short half-life in vivo. In the method of plasmin treatment, although 60 to 70% of the immunoglobulin remain in the form of normal immunoglobulin, the remainder has been converted into low molecular substances which decrease the half-life in vivo of the product as in the case of pepsin treatment. In the case of chemical modification, there is a possibility of the development of fresh antigenicity depending upon the type of modifying radical and other conditions, bringing about the problem of safety when the modified immunoglobulin is to be repeatedly administered.

The fractionation with polyethylene glycol or Pluronics is generally believed to be the most desirable means to recover the immunoglobulin in the form existing in the living body, that is, unmodified and undecomposed immunoglobulin. The procedure has already been disclosed in detail by Polson and Coval [Japanese Patent Application "Kokai" (Laid-open) Nos. 46,814/1975, 91,321/1976 and 20,415/1978]. However, if the polyethylene glycol or Pluronic fractionation is carried out under known conditions, it is possible to obtain an immunoglobulin preparation containing no aggregate-type immunoglobulin and suitable for intravenous injection, but the yield is always low. Therefore, an improvement in the yield has been eagerly awaited.

The present inventors conducted studies to elucidate the cause for the decrease in yield and as a result found that in the step of removing the aggregate-type immunoglobulin at a low concentration of polyethylene glycol or a Pluronic added to the raw immunoglobulin material, the non-aggregate-type immunoglobulin is also removed at the same time. Further, it was also found that an immunoglobulin material containing a comparatively large amount of aggregate-type immunoglobulin is fractionated with polyethylene glycol or a Pluronic, the loss in non-aggregate-type immunoglobulin becomes also large. The present inventors further made an effort to solve the novel technical problem associated with the aforesaid difficulty inherent in the prior art and, as a result, found that the yeild of non-aggregate-type immunoglobulin is remarkably improved by treating the raw immunoglobulin material with an acid to dissociate the aggregate-type immunoblobulin and then subjecting the material to the fractionation with polyethylene glycol or a polyoxyethylene-polyoxypropylene copolymer. Based on this finding, the present invention has been accomplished.

An object of this invention is to provide a process for preparing in a high yield an immunoglobulin suitable for use in intravenous injection from a plasma or Cohn's fraction I+II+III, fraction II+III, fraction II, or fraction III obtained by subjecting a plasma to the Cohn's cold alcohol fractionation.

Other objects and advantages of this invention will become apparent from the following description.

According to this invention there is provided a process for preparing an immunoglobulin suitable for intravenous injection, which comprises treating a plasma or the Cohn's fraction I+II+III, fraction II+III, fraction II, or fraction III obtained by subjecting a plasma to Cohn's cold alcohol fractionation with an acid at pH 3.2 to 5.0 and at 4° to 15° C. for 30 to 180 minutes, adding to the resulting material at pH 4.6 to 5.4 an alkylene oxide polymer or copolymer having a molecular weight of 2,000 to 20,000 to a concentration of 4.5 to 5.5% (W/V), removing an aggregate-type immunoglobulin as a precipitate, and adding again said polymer or copolymer at pH 8.0 to 9.0 to a concentration of 6 to 13% (W/V) to recover as a precipitate a non-aggregate-type immunoglobulin containing substantially no aggregate-type immunoglobulin.

The plasma used as starting material according to this invention is preferably that originated from human blood in view of the problem of antigenicity. The Cohn's plasma fractions I+II+III, II+III, II, and III are substantially α-, β- and γ-globulin (IgG, IgA, IgM). The plasma γ-globulin fraction is obtained by the continuous precipitation with cold ethanol as described in detail in Journal of Clinical Investigation, 23, 417 (1944) and Journal of the American Chemical Society, 68, 479 (1946).

The acid treatment is carried out by keeping the starting material under acidic conditions. By this treatment, the aggregate-type immunoglobulin in the raw material is dissociated first into a non-aggregate type. The acid conditions are pH 3.2 to 5.0, preferably 3.8 to 4.2 and an ionic strength of 0.002 to 0.30, preferably 0.10 to 0.20. Other pH conditions are undesirable because if pH is below 3.2, denaturation of the protein will take place, while if it is above 5.0, the said dissociation of the aggregate-type immonoglobulin becomes insufficient. The concentration of protein is not critical, but is preferably 2 to 10% (W/V), because of the ease of operation. The temperature of acid treatment is 4° to 15° C. Other temperatures are not desirable, because if the temperature is below 4° C., the aforesaid dissociation will be insufficient, while if it exceeds 15° C., decomposition of the protein will take place. The duration of the acid treatment is 30 to 180 minutes. If the duration of treatment is shorter than 30 minutes, the aforesaid dissociation becomes insufficient, while too long a duration of treatment is the waste of time and even sometimes gives unfavorable results. The acids used for the treatment include inorganic acids such as hydrochloric acid and phosphoric acid and organic acids such as acetic acid and citric acid.

After such acid treatment as described above, a fractionation is preformed by using an alkylene oxide polymer or copolymer having a molecular weight of 2,000 to 20,000, to produce a high-purity non-aggregate-type immunoglobulin in a high yield. The alkylene group of the alkylene oxide polymer used in the fractionation is that having 1 to 4 carbon atoms such as methylene, ethylene, propylene or butylene group. The alkylene oxide copolymers include copolymers of two or more alkylene oxides such as polyoxyethylene-polyoxypropylene copolymer.

The present inventors found that in the fractionation using an alkylene oxide polymer or copolymer having a molecular weight of 2,000 to 20,000, the pH conditions are a very important factor and the yield and purity of the immunoglobulin are markedly improved only in a very limited pH range of from 4.6 to 5.4, preferably from 4.8 to 5.2. This is clearly shown also by the experimental results (Table 1) obtained by dissolving a fraction II+III paste in 0.6% aqueous sodium chloride solution to a protein concentration of 5%, treating the resulting solution with an acid at pH 3.5 and 10° C. for 60 minutes, fractionating the solution with polyethylene glycol (5% in concentration) at varied pH in the range of 4.0 to 6.0, and determining the yield and purity of the non-aggregate-type immunoglobulin.

TABLE 1

| pH | pH conditions in polyethylene glycol fractionation. | |
|---|---|---|
| | IgG recovery, % | IgG purity, % |
| 4.1 | 60 | 35 |
| 4.3 | 58 | 60 |
| 5.0 | 70 | 98 |
| 5.5 | 45 | 95 |
| 6.0 | 10 | 93 |

When a polyoxyethylene-polyoxypropylene copolymer of an average molecular weight of 15,000 is used in place of the polyethylene glycol, a higher yield and higher purity of the non-aggregate-type immunoglobulin are obtained also under the above pH conditions than those obtained under other pH conditions.

The above polymer or copolymer is added to the starting material to a concentration of 4.5 to 5.5%, preferably 5% (W/V) and the precipitated impurities, e.g. aggregate-type immunoglobulin, are removed by a customary means, e.g. centrifuging (1,000–5,000 rpm). To the supernatant thus fractionated, is further added the above polymer or copolymer to a concentration of 6 to 13%. By adjusting pH to 8.0 to 9.0, the intended non-aggregate-type immunoglobulin is precipitated and can be recovered by a customary means, e.g. centrifuging (1,000 to 5,000 rpm). The recovery of the intended product under the above conditions is 60% or more. The precipitate which was formed is again dissolved, for example, in a physiological saline or a 0.02 M acetate buffer solution admixed with 0.6% of sodium chloride, 2% of mannit and 1% of albumin, and the resulting solution is passed through a bacterial filter to obtain an intravenous immunoglobulin solution suitable for clinical use. The immunoglobulin in this solution shows no change in its properties upon dispensing the solution in small portions into vials and lyophilizing. Accordingly, when the product is intended for long-term storage, it can be made into the form of lyophilized preparation.

The immunoglobulin prepared by the present process contains substantially no aggregate-type immunoglobulin and the anticomplementary activity is less than 20 units, as assayed on a solution of 5% in concentration, the purity as IgG being 90% or above.

The invention is illustrated below in detail with reference to Examples, but the invention is not limited thereto.

In Examples, the recovery of immunoglobulin was determined by the single immunodiffusion and the purity by the electrophoresis using a cellulose acetate membrane. The anticomplementary activity was assayed by the method of Kobat and Mayer [Experimental Immunochemistry, p 225 (1961)] and the method of Nishioka and Okada ["Biochemistry of Immunity", p 103 (1971), Kyoritsu Publishing Company].

EXAMPLE 1

The Cohn's fraction II+III paste (1 kg) obtained by the cold alcohol fractionation was dissolved in 10 liters of a 0.6% aqueous sodium chloride solution. The solution was adjusted to pH 3.8 with 1 N hydrochloric acid and stirred at 4° C. for 60 minutes to effect acid treatment. To the solution was added 500 g of polyethylene glycol (average molecular weight 4,000). While allowing the polyethylene glycol to dissolve, pH of the solution was gradually increased with 1 N aqueous sodium hydroxide solution. As soon as the pH reached 5.0, the precipitate was removed by centrifugation (4,000 rpm) to obtain a clear supernatant. The recovery of IgG in the supernatant was 85% based on the fraction II+III and the purity of IgG was 97%. To the supernatant was added another 500 g of polyethylene glycol (molecular weight 4,000). While being stirred mildly, the supernatant was adjusted to pH 8.5 with 1 N aqueous sodium hydroxide solution. The immunoglobulin precipitated under the above conditions was recovered by centrifugation (4,000 rpm). The whole of the recovered precipitate was dissolved in a 0.02 M acetate buffer solution (pH 6.6) containing 1% of human albumin and using the same solvent the concentration was adjusted to 5%. The solution was sterilized by passing through a Millipore filter (Millipore Co.) and aseptically dispensed in small containers. One half of the dispensed liquor was immediately lyophilized to yield a dry preparation.

The ultimate yield of IgG from the starting material was 84%, as contrasted with 63% when the acid treatment at pH 3.8 to the starting material was omitted. The purity was 95%, excluding the albumin which was added afterwards. The anticomplementary activities (at a protein concentration of 5%) of the liquid preparation and the solution of lyophilized preparation were found to be 14 and 16, respectively.

A 5% solution was administered to 5 mice, about 20 g in body weight, at a dose of 1 ml per mouse. Neither decrease in body weight nor any anomaly in Piloerection was noted during an observation period of one week. The lyophilized preparation was tested after one year of storage at 4° C., but no change in solubility and anticomplementary activity was observed as compared with the initial preparation.

EXAMPLE 2

A Cohn's fraction II paste (500 g) obtained by the cold ethanol fractionation was dissolved in 10 liters of a 0.1% sodium chloride solution. Immunoglobulin containing no aggregate type was recovered from the solution in a manner similar to that in Example 1. The yield in terms of IgG was 80%, as contrasted with 62% when the acid treatment (pH 3.8) was omitted. The purity was 97%.

In a manner similar to that in Example 1, the immunoglobulin obtained above was dissolved in a 0.5% sodium chloride solution to a protein concentration of 5%. After addition of 1% of mannit, the solution was passed through a bacterial filter and lyophilized. The lyophilized preparation was dissolved in distilled water for injection to a protein concentration of 5%. The anticomplementary activity at this concentration was found to be 13.

EXAMPLE 3

The procedure of Example 1 was repeated, except that the polyethylene glycol (average molecular weight 4,000) was replaced by the same amount of a polyoxyethylene-polyoxypropylene copolymer (average molecular weight 15,000). The immunoglobulin was recovered with the same results as in Example 1.

What is claimed is:

1. A process for preparing an immunoglobulin suitable for intravenous injection, which consists essentially of treating a plasma or the Cohn's fraction I+II+III, fraction II+III, fraction II, or fraction III obtained by subjecting a plasma to Cohn's cold alcohol fractionation with an acid at pH 3.2 to 5.0 and at 4° to 15° C. for 30 to 180 minutes, adding to the resulting material at pH 4.6 to 5.4 an alkylene oxide polymer or copolymer having a molecular weight of 2,000 to 20,000 to a concentration of 4.5 to 5.5% (W/V), removing an aggregate-type immunoglobulin as a precipitate, and adding again said polymer or copolymer at pH 8.0 to 9.0 to a concentration of 6 to 13% (W/V) to recover as a precipitate a non-aggregate-type immunoglobulin containing substantially no aggregate-type immunoglobulin.

2. A process according to claim 1 consisting of the stated steps.

3. In a process for preparing an immunoglobulin suitable for intravenous injection, which comprises adding to a plasma or the Cohn's fraction I+II+III, fraction II+III, fraction II, or fraction III obtained by subjecting a plasma to Cohn's cold alcohol fractionation at pH 4.6 to 5.4 an alkylene oxide polymer or copolymer having a molecular weight of 2,000 to 20,000 to a concentration of 4.5 to 5.5% (W/V), removing an aggregate-type immunoglobulin as a precipitate, and adding again said polymer or copolymer at pH 8.0 to 9.0 to a concentration of 6 to 13% (W/V) to recover as a precipitate a non-aggregate-type immunoglobulin containing substantially no aggregate-type immunoglobulin, the improvement which comprises treating the plasma or the Cohn's fraction I+II+III, fraction II+III, fraction II, or fraction III with an acid at pH 3.2 to 5.0 and at 4° to 15° C. for 30 to 180 minutes, before the addition of the alkylene oxide polymer or copolymer.

4. A process according to claim 3, wherein the protein concentration in the acid treatment is 2 to 10% (W/V).

5. A process according to claim 3, wherein the acid is hydrochloric acid, phosphoric acid, acetic acid, or citric acid.

6. A process according to claim 3, wherein the plasma is that originated from human blood.

7. A process according to claim 3, wherein the alkylene oxide polymer is that having methylene, ethylene, propylene or butylene group.

8. A process according to claim 3, wherein the alkylene oxide copolymer is a polyoxyethylene-polyoxypropylene copolymer.

* * * * *